(12) United States Patent
Wright et al.

(10) Patent No.: US 9,630,248 B2
(45) Date of Patent: Apr. 25, 2017

(54) METHOD OF MANUFACTURING AN ARTICLE BY HOT PRESSING AND ULTRASONICALLY INSPECTING THE ARTICLE

(71) Applicant: ROLLS-ROYCE PLC, London (GB)

(72) Inventors: David Cameron Wright, Loughborough (GB); Daniel Clark, Belper (GB)

(73) Assignee: ROLLS-ROYCE plc, London (GB)

( * ) Notice: Subject to any disclaimer, the term of this patent is extended or adjusted under 35 U.S.C. 154(b) by 469 days.

(21) Appl. No.: 14/483,814

(22) Filed: Sep. 11, 2014

(65) Prior Publication Data

US 2015/0098854 A1    Apr. 9, 2015

(30) Foreign Application Priority Data

Oct. 8, 2013 (GB) .................................. 1317757.1

(51) Int. Cl.
*B22F 3/15* (2006.01)
*B23K 20/02* (2006.01)
(Continued)

(52) U.S. Cl.
CPC .................. *B22F 3/15* (2013.01); *B22F 3/24* (2013.01); *B22F 7/06* (2013.01); *B22F 7/062* (2013.01);
(Continued)

(58) Field of Classification Search
CPC ............ G01N 29/11; G01N 2291/044; G01N 29/04–29/043; B22F 3/15
(Continued)

(56) References Cited

U.S. PATENT DOCUMENTS 4,233,720 A    11/1980 Rozmus
7,650,790 B2    1/2010 Wright
(Continued)

OTHER PUBLICATIONS

Atkinson, H. V. et al. "Fundamental Aspects of Hot Isostatic Pressing: An Overview" Metallurgical and Materials Transactions A: Physical Metallurgy & Materials Science, ASM International, Materials Park. vol. 31A, No. 12. Dec. 1, 2000 pp. 2981-3000.
(Continued)

*Primary Examiner* — Jessee Roe
*Assistant Examiner* — Jeremy Jones
(74) *Attorney, Agent, or Firm* — Oliff PLC

(57) ABSTRACT

A method of manufacturing an article by hot pressing and ultrasonically inspecting the article comprises forming and filling a canister with powder material and evacuating and sealing the canister. Heat and pressure are applied to the canister to consolidate the powder material to form the article. The article within the canister is ultrasonically inspected by moving a transducer over the whole of the canister. The position of an interface between the article and the canister, and the thickness of the canister, at each position on the surface of the canister and if there are defects within the article are determined. The canister is then removed from the article by machining the canister using a machining tool, the movement of the tool is controlled such that at each position of the canister the tool removes the determined thickness of the canister for the corresponding position on the surface of the canister.

22 Claims, 8 Drawing Sheets

(51) Int. Cl.
- *B22F 7/06* (2006.01)
- *G01N 29/04* (2006.01)
- *G01N 29/11* (2006.01)
- *B22F 3/24* (2006.01)
- *B22F 7/08* (2006.01)
- *F23R 3/00* (2006.01)
- *C22C 49/08* (2006.01)
- *C22C 49/11* (2006.01)

(52) U.S. Cl.
CPC ............. *B22F 7/08* (2013.01); *B23K 20/021* (2013.01); *F23R 3/00* (2013.01); *G01N 29/043* (2013.01); *G01N 29/11* (2013.01); *B22F 2201/20* (2013.01); *B22F 2998/00* (2013.01); *B22F 2998/10* (2013.01); *B22F 2999/00* (2013.01); *C22C 49/08* (2013.01); *C22C 49/11* (2013.01); *F23R 2900/00018* (2013.01); *G01N 2291/02458* (2013.01); *G01N 2291/044* (2013.01); *G01N 2291/2693* (2013.01)

(58) Field of Classification Search
USPC .......................................................... 228/104
See application file for complete search history.

(56) References Cited

U.S. PATENT DOCUMENTS

| | | |
|---|---|---|
| 2006/0266119 A1 | 11/2006 | Cobb |
| 2007/0020135 A1* | 1/2007 | Jackson .................... B22F 3/14 419/29 |
| 2010/0263450 A1 | 10/2010 | Bobrek |
| 2011/0038748 A1 | 2/2011 | Channel |
| 2014/0260625 A1* | 9/2014 | Escobar-Ruiz .... G01N 29/4454 73/588 |

OTHER PUBLICATIONS

Feb. 23, 2015 Search Report Issued in EP Application No. 14184381.

Search Report issued in British Patent Application No. 1317757.1 dated Apr. 8, 2014.

* cited by examiner

METHOD OF MANUFACTURING AN ARTICLE BY HOT PRESSING AND ULTRASONICALLY INSPECTING THE ARTICLE

FIELD OF THE INVENTION

The present invention relates to a method of manufacturing an article by hot pressing and ultrasonically inspecting the article. The present invention relates in particular to a method of manufacturing an article by hot pressing powder material to consolidate and diffusion bond the powder material together to form the article and ultrasonically inspecting the article or relates to a method of manufacturing an article by hot pressing a plurality of components to diffusion bond the components together and ultrasonically inspecting the article or relates to a method of manufacturing an article by hot pressing powder material and at least one component to consolidate the powder material and diffusion bond the powder material and at least one component together and ultrasonically inspecting the article. In particular the method of manufacturing an article by hot pressing uses hot isostatic pressing.

BACKGROUND TO THE INVENTION

Hot pressing, or hot isostatic pressing, is used to manufacture an article, or component, by consolidating and diffusion bonding powder material together to form the article or component. Hot pressing, or hot isostatic pressing, is used to diffusion bond two or more components together to form an article and in addition hot pressing, or hot isostatic pressing is also used to manufacture an article by consolidating and diffusion bonding powder material and one or more components together to form an article.

Hot isostatic pressing of powder materials to manufacture an article involves initially forming a canister which defines the shape of the article to be manufactured. The canister is filled with powder material, the canister is evacuated to remove gases from the canister and then the canister is sealed. The sealed canister is then hot isostatically pressed to consolidate the powder material within the canister and to diffusion bond the powder material together to form the article. During the hot isostatic pressing process the particles of the powder material are initially deformed to fill the inter-particle spaces, or voids, and then the particles of the powder material are diffusion bonded together. The canister is then removed from the article by machining, by dissolving the canister in acid or by a combination of machining and dissolving in acid. The article is subsequently ultrasonically inspected to ensure that there are no defects, or flaws, in the article, e.g. voids, unbounded regions or contaminants.

U.S. Pat. No. 4,233,720 discloses a method of manufacturing an article by hot isostatic pressing and ultrasonically inspecting the article. U.S. Pat. No. 4,233,720 discloses that after the article has been manufactured by hot isostatic pressing the article is ultrasonically inspected while the article is within the canister to detect defective articles at an early stage before additional processing costs are incurred. In particular the canister is machined so that two opposite surfaces are parallel and the surfaces are ground to a suitable smoothness for ultrasonically inspecting the article within the canister. After ultrasonic inspection of the article within the canister, the canister is removed by etching in acid or by machining. The article is then machined to final shape.

There is a requirement to manufacture articles from powder material using hot pressing, or hot isostatic pressing, to net shape or near net shape, so that after the canister has been removed no, or only minimal, machining of the article is required.

A problem associated with the use of acids is that the use of acids to remove, dissolve, the canister may be precluded by environmental legislation. A further problem associated with acids is that the acids used to remove the canister may also cause damage to the article and this is of particular concern if the article is a ferritic steel or the article is a bi-metallic for corrosion resistance.

An additional problem associated with machining is that the use of machining to remove the canister may result in damage to the article because the position of the interface between the canister and the article and the positions of features of the article are not known after the hot pressing, or hot isostatic pressing, process. The position of the interface between the canister and the article after consolidation of the powder material is not known accurately because of process variations in the shrinkage of the particles of the powder material and the collapse of the canister as the inter-particle spaces, or voids, are filled by the deformation of the particles of the powder material.

STATEMENTS OF INVENTION

Therefore the present invention seeks to provide a method of manufacturing an article by hot pressing and ultrasonically inspecting the article which reduces or overcomes the above mentioned problem.

Accordingly the present invention provides a method of manufacturing an article by hot pressing and ultrasonically inspecting the article comprising the steps of:—
(a) forming a canister,
(b) filling the canister with powder material, filling the canister with a plurality of components or filling the canister with powder material and at least one component,
(c) evacuating the canister,
(d) sealing the evacuated canister,
(e) applying heat and pressure to the canister to consolidate and diffusion bond the powder material together to form the article, to diffusion bond the components together to form the article or to consolidate the powder material and diffusion bond the powder material and the at least one component together to form the article,
(f) ultrasonically inspecting the article within the canister by moving at least one ultrasonic transducer over the whole of an external surface of the canister,
(g) determining the position of an interface between the article and the canister at each position on the external surface of the canister,
(h) determining if there are any defects within the article,
(i) determining the thickness of the canister at each position on the surface of the canister,
(j) removing the canister from the article by machining the canister using a machine tool, and
(k) controlling the movement of the machine tool over the canister such that at each position of the canister the machine tool removes the determined thickness of the canister for the corresponding position on the external surface of the canister.

The hot pressing may comprise hot isostatic pressing. The hot isostatic pressing may comprise hot isostatic pressing at a temperature in the range of 800 to 950° C. and a pressure of at least 70 MPa.

The canister may be machined from the article using a milling tool and/or a grinding tool.

The powder material may comprise a powder metal or a powder alloy.

The component may be a metal or an alloy.

The powder material and the component may have the same composition.

The powder material may be a nickel alloy, a titanium alloy, a ferritic steel, an austenitic stainless steel or a duplex stainless steel. The component may be a nickel alloy, a titanium alloy, a ferritic steel, an austenitic stainless steel or a duplex stainless steel.

The powder metal may be nickel, titanium, copper or aluminium. The component may be nickel, titanium, copper or aluminium.

The powder material may be a combination of two or more metal powders or two or more alloy powders or a combination of an alloy powder and a metal powder to form a bi-metallic, e.g. a copper and aluminium bi-metallic.

Reinforcing fibres may be provided in the canister with the powder material to form a fibre reinforced article. The fibre reinforced article may comprise a metal matrix composite, e.g. a titanium metal matrix composite, or a ceramic matrix composite.

The component may be at least one a wire or at least one block. The block may have been previously formed from powder material.

Reinforcing fibres may be provided in the canister with the at least one wire to form a fibre reinforced article. The fibre reinforced article may comprise a metal matrix composite, e.g. titanium metal matrix composite, or a ceramic matrix composite.

The article may be a casing and the casing may be a gas turbine engine or turbomachine casing.

Step (f) may comprise providing a single ultrasonic transducer, transmitting an ultrasonic signal from the ultrasonic transducer through the canister into the article and receiving an ultrasonic signal returning from the article through the canister at the single ultrasonic transducer.

Step (f) may comprise providing a first ultrasonic transducer and a second ultrasonic transducer, transmitting an ultrasonic signal from the first ultrasonic transducer through the canister into the article and receiving an ultrasonic signal from the article through the canister at the second ultrasonic transducer.

Step (f) may comprise providing a first ultrasonic transducer comprising a multiple element one dimensional array transducer and a second ultrasonic transducer comprising a multiple element one dimensional array transducer or a first ultrasonic transducer comprising a multiple element two dimensional array transducer and a second ultrasonic transducer comprising a multiple element two dimensional array transducer.

Step (f) may comprise providing a piezoelectric transducer or a magnetostrictive transducer.

Step (f) may comprise using frequencies in the range of 1 to 40 MHz.

Step (k) may comprise providing a feedback sensor on the machining tool.

The present invention also provides a method of inspecting and removing an article produced by hot pressing from a canister comprising the steps of:—
(a) ultrasonically inspecting an article produced by hot pressing within a canister by moving at least one ultrasonic transducer over the whole of an external surface of the canister,
(b) determining the position of an interface between the article and the canister at each position on the external surface of the canister,
(c) determining if there are any defects within the article,
(d) determining the thickness of the canister at each position on the surface of the canister,
(e) removing the canister from the article by machining the canister using a machine tool, and
(f) controlling the movement of the machine tool over the canister such that at each position of the canister the machine tool removes the determined thickness of the canister for the corresponding position on the external surface of the canister.

BRIEF DESCRIPTION OF THE DRAWINGS

The present invention will be more fully described by way of example with reference to the accompanying drawings, in which:—

DETAILED DESCRIPTION

Figure 1:
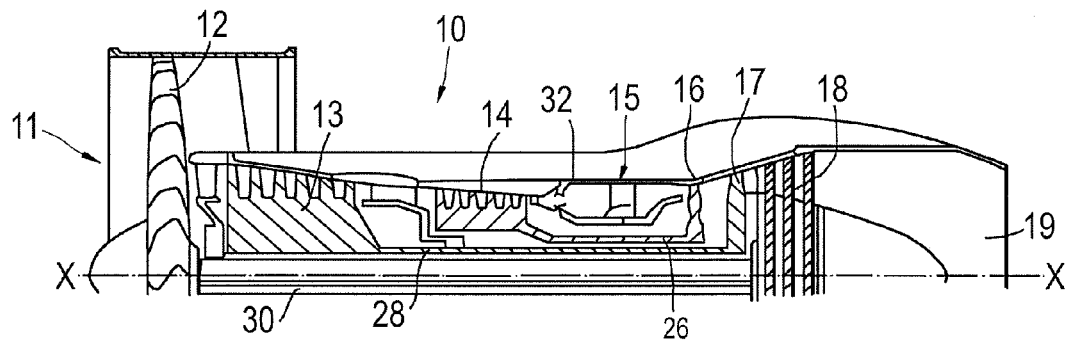
FIG. 1 is partially cut away view of a turbofan gas turbine engine having a combustor casing manufactured using a method according to the present invention.

A turbofan gas turbine engine 10, as shown in FIG. 1, comprises in flow series an intake 11, a fan 12, an intermediate pressure compressor 13, a high pressure compressor 14, a combustion chamber 15, a high pressure turbine 16, an intermediate pressure turbine 17, a low pressure turbine 18 and an exhaust 19. The high pressure turbine 16 is arranged to drive the high pressure compressor 14 via a first shaft 26. The intermediate pressure turbine 17 is arranged to drive the intermediate pressure compressor 13 via a second shaft 28 and the low pressure turbine 18 is arranged to drive the fan 12 via a third shaft 30. In operation air flows into the intake 11 and is compressed by the fan 12. A first portion of the air flows through, and is compressed by, the intermediate pressure compressor 13 and the high pressure compressor 14 and is supplied to the combustion chamber 15. Fuel is injected into the combustion chamber 15 and is burnt in the air to produce hot exhaust gases which flow through, and drive, the high pressure turbine 16, the intermediate pressure turbine 17 and the low pressure turbine 18. The hot exhaust gases leaving the low pressure turbine 18 flow through the exhaust 19 to provide propulsive thrust. A second portion of the air bypasses the main engine to provide propulsive thrust.

The fan 12, the intermediate pressure compressor 13, the high pressure compressor 14, the combustor 15, the high pressure turbine 16, the intermediate pressure turbine 17 and the low pressure turbine 18 are each enclosed by a respective casing.

Figure 2:
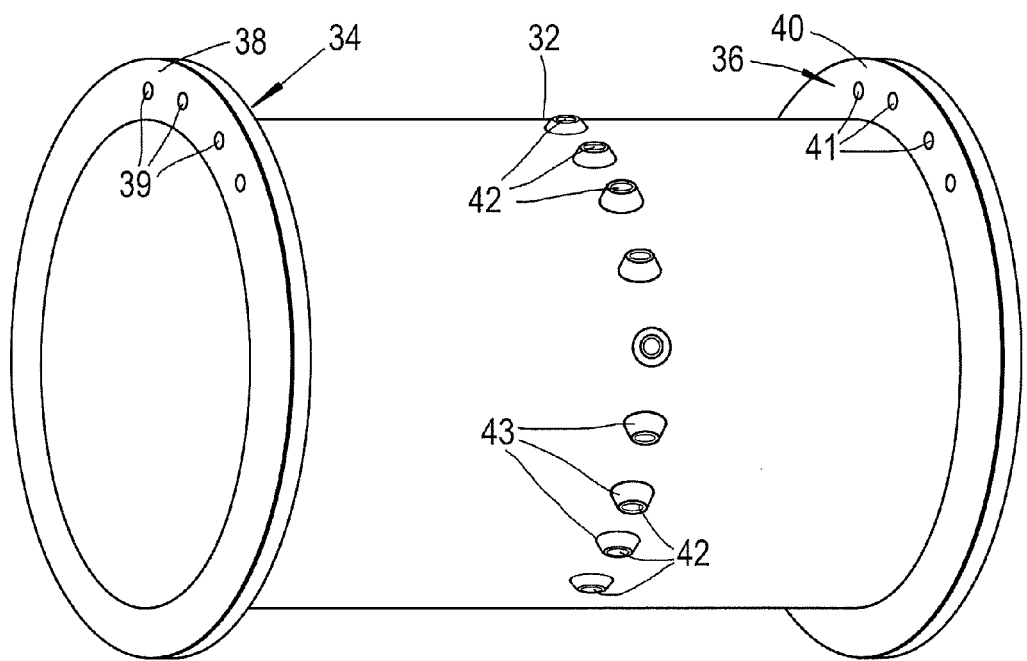
FIG. 2 is an enlarged perspective view of a combustor casing manufactured using a method according to the present invention.

A combustor casing 32 is shown more clearly in FIG. 2 and the combustor casing 32 comprises an annular radially outwardly extending flange 38 at an upstream end 34 of the combustor casing 32 and an annular radially outwardly extending flange 40 at a downstream end 36 of the combustor casing 32. The flanges 38 and 40 enable the combustor casing 32 to be secured to a casing of the adjacent high pressure compressor 14 and a casing of the high pressure turbine 16. The flanges 38 and 40 have apertures 39 and 41 respectively for bolts and nuts or other suitable fasteners to be used to secure the adjacent casings together. The combustor casing 32 also has a plurality of circumferentially spaced apertures 42, which have associated bosses 43 and threaded blind holes, to allow fuel injectors to be inserted into the combustion chamber 15.

The combustor casing 32 is manufactured by hot isostatic pressing of a powder material, e.g. a powder metal or powder alloy. The powder alloy may be a nickel-base superalloy, for example RR1000.

Figure 3:
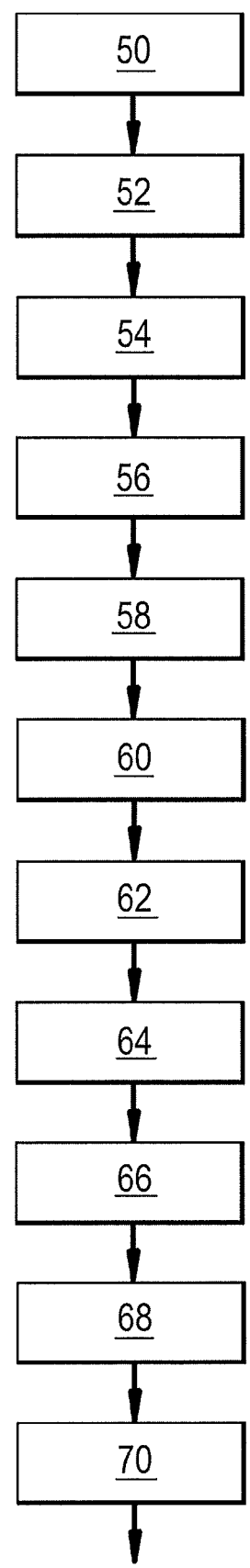
FIG. 3 is a flow diagram of a method of manufacturing a combustor casing according to the present invention.

A method of manufacturing an article, for example the combustor casing 32, by hot isostatic pressing and ultrasonically inspecting the article, the combustor casing 32, is illustrated using the flow diagram in FIG. 3. The method of manufacturing the article, the combustor casing 32, comprises the steps of forming a canister 50, filling the canister with powder material 52, evacuating the canister 54, sealing the evacuated canister 56 and applying heat and pressure to the sealed canister to consolidate and diffusion bond the powder material together to form the article within the canister 58. The method of manufacturing the article, the combustor casing 32, further comprises the steps of ultrasonically inspecting the article within the canister 60 by moving at least one ultrasonic transducer over the whole of an external surface of the canister, determining the position of an interface between the article and the canister at each position on the external surface of the canister 62, determining if there are any defects within the article 64, determining the thickness of the canister at each position on the surface of the canister 66, removing the canister from the article by machining the canister using a machine tool 68, and controlling the movement of the machine tool over the canister such that at each position of the canister the machine tool removes the determined thickness of the canister for the corresponding position on the external surface of the canister 70.

Figure 4:
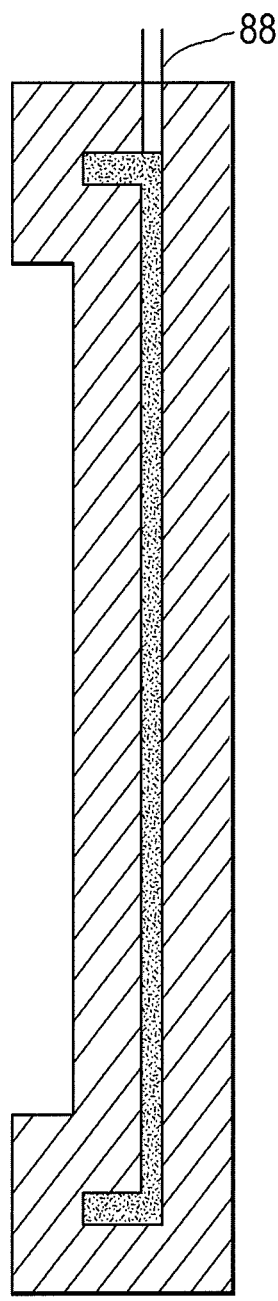
FIG. 4 is an enlarged longitudinal cross-sectional view of a canister for manufacturing a combustor casing using a method according to the present invention.
Figure 4:
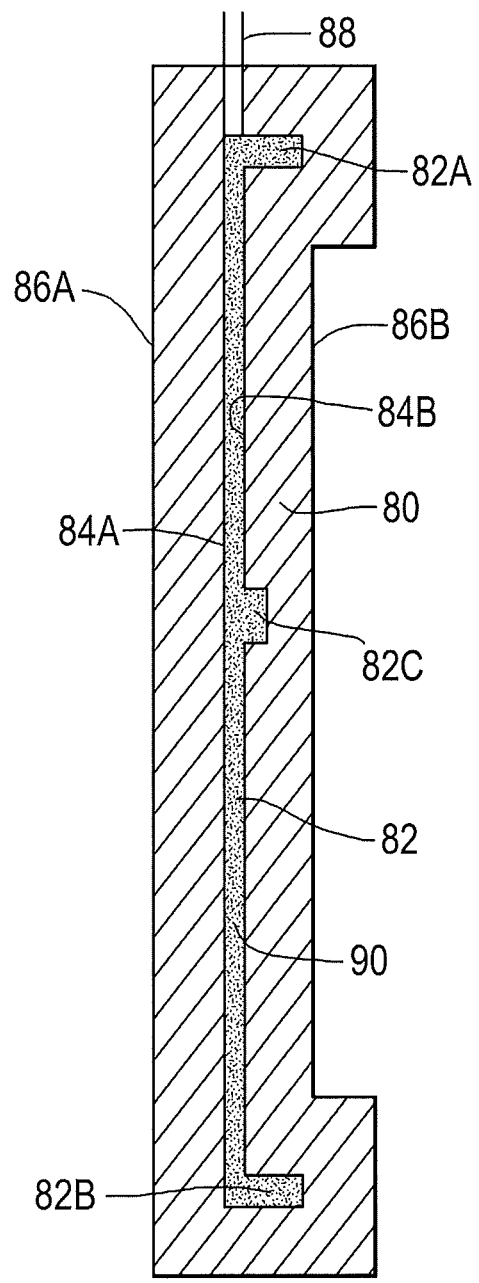

A canister 80, as shown in FIG. 4, is formed to manufacture the article, for example the combustor casing 32. The canister 80 is generally annular, is hollow and defines a generally annular chamber 82 which has sub chambers 82A, 82B and 82C which define the flanges 38, 40 and bosses 43 and other features of the combustor casing 32. The canister 80 is a multi-part canister and the adjacent parts of the canister are sealed together. The parts of the canister 80 are machined so that the annular chamber 82 has the required radially inner internal shape 84A, the required radially outer internal shape 84B and the parts of the canister have the required radially inner external shape 86A and the required radially outer external shape 86B so that after the hot isostatic pressing step the combustor casing 32 has the required shape and dimensions.

The canister 80 in FIG. 4 is also provided with one or more pipes 88 and powder material, powder metal, 90 is supplied through the one or more pipes 88 into the annular chamber 82 within the canister 80. After the annular chamber 82, within the canister 80, is completely filled with powder material, powder metal or powder alloy, a leak check is performed by applying a vacuum to the canister 80 and determining if any gas leaks into the canister 80 by measuring the pressure within the canister 80 to determine if the pressure rises within the canister 80. If the canister 80 passes the leak check the pipes 88 are sealed by crimping and then the pipes 88 are further sealed by welding, e.g. spot welding etc.

The evacuated and sealed canister 80 containing power material, powder metal or powder alloy, 90 is then placed in a HIP vessel and hot isostatically pressed at a high temperature and high pressure for a predetermined time to consolidate the powder material, powder metal or powder alloy, and to diffusion bond the powder material, powder metal or powder alloy, particles together to form a powder material, powder metal or powder alloy, combustor casing 32.

The canister 80 containing the powder material, powder metal or powder alloy, combustor casing 32 is then removed from the HIP vessel and the canister 80 and combustor casing 32 within the canister 80 are ultrasonically inspected. The canister 80 is initially prepared for ultrasonic inspection by machining the external surfaces of the canister 80 such that they are rectilinear and in the case of the canister 80 for the combustor casing 32 the canister 80 comprises a series of parallel straight lines extending axially from end to end of the canister on the radially inner external surface of the canister 80, similarly comprises a series of parallel straight lines extending axially from end to end of the canister on the radially outer external surface of the canister 80 and a series of straight lines extending radially at the ends of the canister 80. Any suitable machining process may be used to prepare the external surfaces of the canister 80 for ultrasonic inspection.

Figure 5:
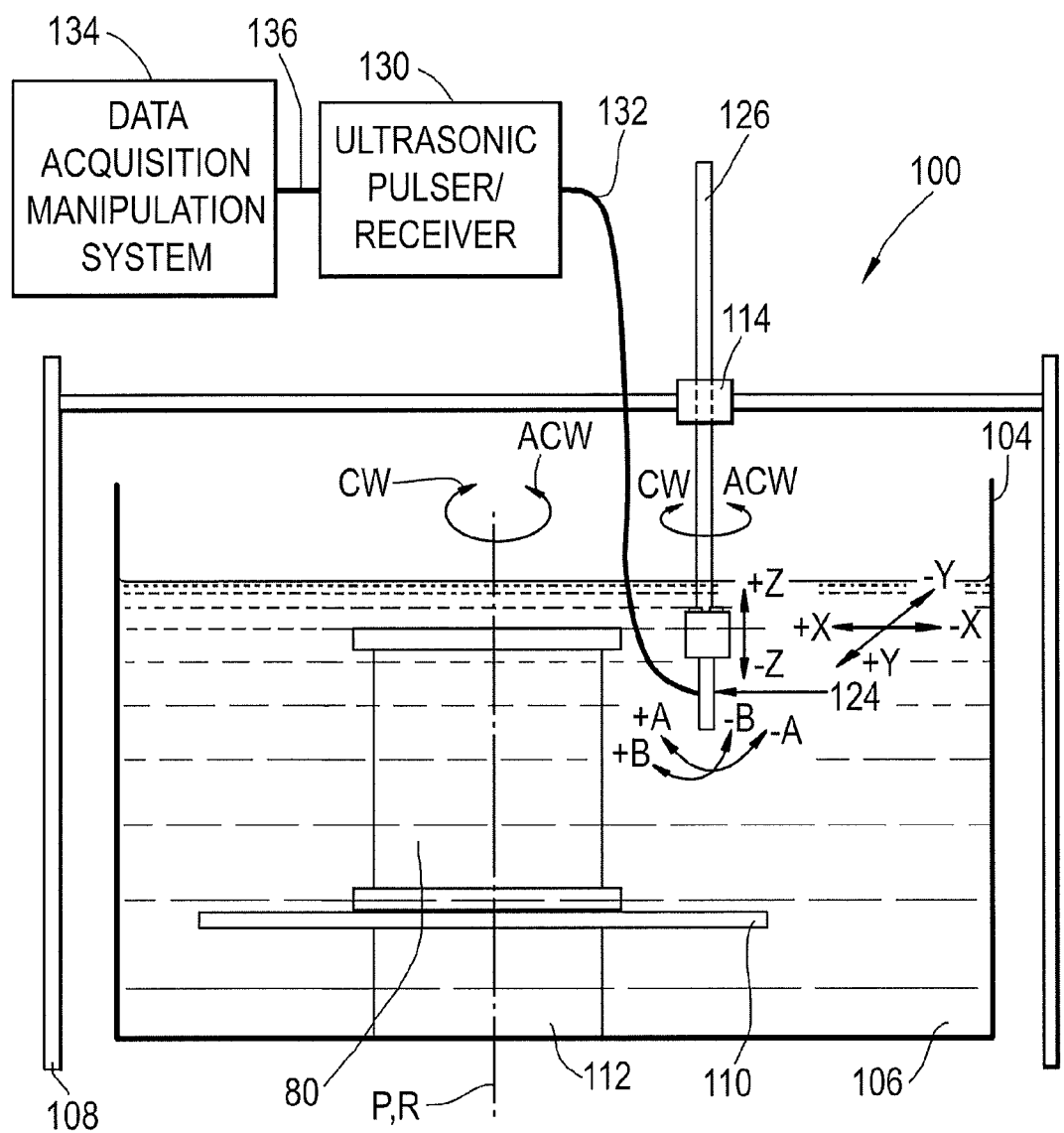
FIG. 5 is a side view of an apparatus for ultrasonically inspecting a combustor casing using a method according to the present invention.
Figure 6:
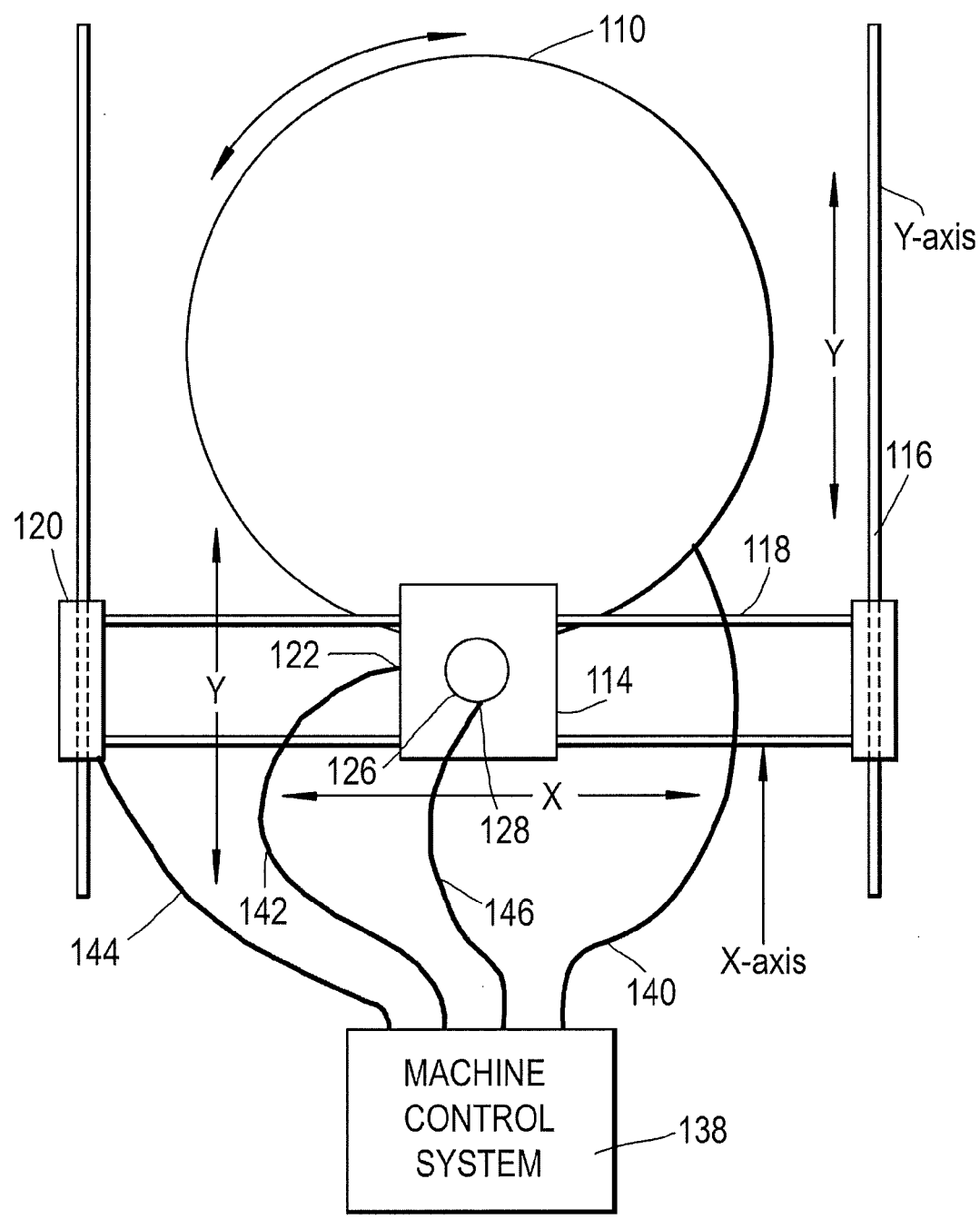
FIG. 6 is a plan view of the apparatus for ultrasonically inspecting a combustor casing shown in FIG. 5.

An apparatus 100, as shown in FIGS. 5 and 6, for ultrasonically inspecting the canister 80 and combustor casing 32, which are generally rotationally symmetrical components, comprises a tank 104 containing a liquid 106 and a frame 108. A rotatable turntable 110 and a device 112 are provided to rotate the turntable 110. The device 112 to rotate the turntable 110 is preferably a motor directly driving the turntable 110, but alternatively the device 112 to rotate the turntable 110 may be a motor indirectly driving the turntable 110 via a belt, or a chain. The canister 80 containing the combustor casing 32 is immersed in the liquid 106 in the tank 104 and is positioned on the turntable 110 such that the axis of rotational symmetry P of the canister 80 and combustor casing 32 coincides with the axis of rotation R of the turntable 110.

The frame 108 is provided with a carriage 114, which is movable along first and second tracks 116 and 118 on the frame 108 and devices 120 and 122 are provided to move the carriage 114 along the tracks 116 and 118. The tracks 116 and 118 are arranged perpendicularly to enable movement in a Y-axis and an X-axis respectively. The carriage 114 carries an ultrasonic transducer 124 on a member 126 and a device 128 is provided to move the member 126 towards or away from the turntable 110 and canister 80 in a direction perpendicularly to the tracks 116 and 118 in a Z-axis. The member 126 may also be rotated. The devices 120, 122 and 128 to move the carriage 114 and to move the member 126 may be motors or hydraulic, pneumatic or electric pistons and cylinders etc.

The ultrasonic transducer 124 transmits and receives ultrasonic signals and the ultrasonic transducer 124 is electrically connected to an ultrasonic signal pulser and receiver 130 by an electric cable 132 and is electrically connected to an ultrasonic signal analyser and display 134 by the ultrasonic signal pulser and receiver 130 and electric cables 132 and 136. The ultrasonic signal analyser and display 134 comprises a computer e.g. a personal computer. The ultrasonic transducer 124 may also have A and B normalising axes. The ultrasonic pulser and receiver 130, sometimes called an ultrasonic flaw detector, comprises a very high gain amplifier and a timing trigger. The apparatus also comprises a controller 138 electrically connected to the motor 112 via a cable 140, electrically connected to the motor 122 via a cable 142, electrically connected to the motor 120 via a cable 144 and electrically connected to the motor 128 via a cable 146 to provide signals to move the carriage 114 and the member 126.

Figure 7:
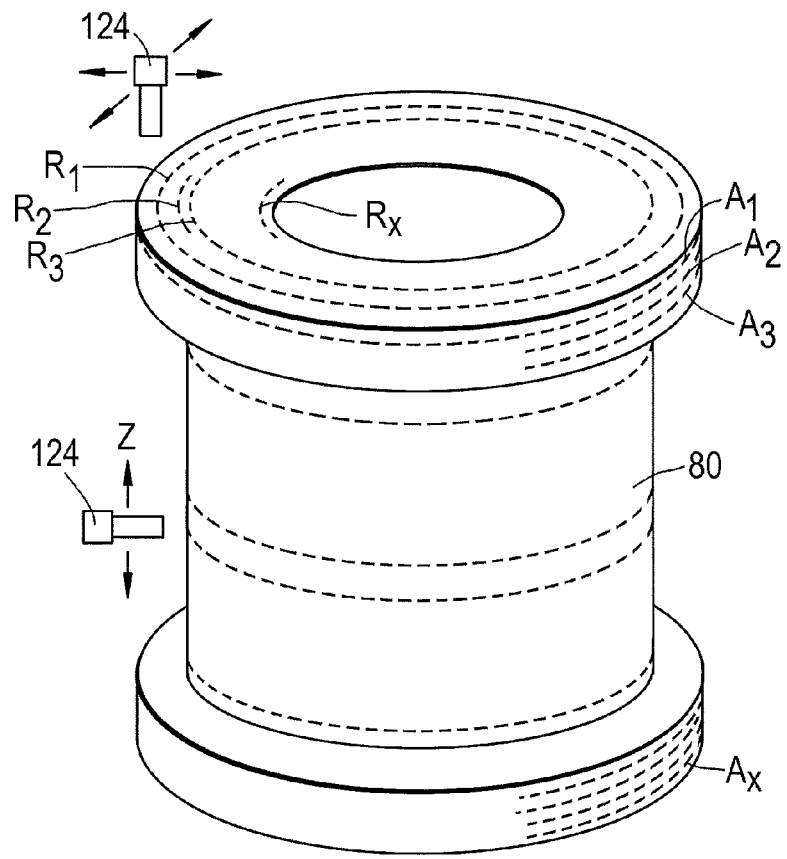
FIG. 7 is a perspective view of the apparatus for ultrasonically inspecting a combustor casing shown in FIGS. 5 and 6 illustrating the ultrasonic inspection process.

In operation, as shown in FIG. 7, the controller 138 sends signals to the motor 112 such that the turntable 110 is rotated about its axis of rotation R for one complete revolution while the carriage 114 and transducer 124 are at a first radial position $R_1$ at an end of the canister 80. During the rotation of the turntable 110 the ultrasonic transducer 124 is supplied with ultrasonic signals from the ultrasonic signal pulser and receiver 130 and the ultrasonic transducer 124 injects ultrasonic signals through the liquid 106 and into the canister 80. The ultrasonic transducer 124 detects reflected ultrasonic signals from the canister 80 and also from the combustor casing 32 within the canister 80 and supplies ultrasonic signals to the ultrasonic signal analyser 134 via the ultrasonic signal pulser and receiver 130. The ultrasonic signal analyser 134 stores the ultrasonic signals.

The controller 138 sends signals to the motors 120 and/or 122 such that the carriage 114 is moved along the tracks 116 and 118 on the frame 108 and the turntable 110 is rotated about its axis of rotation for one complete revolution while the carriage 114 and transducer 124 are at a second radial position $R_2$ at the end of the canister 80. During the rotation of the turntable 110 the ultrasonic transducer 124 is supplied with ultrasonic signals from the ultrasonic signal pulser and receiver 130 and the ultrasonic transducer 124 injects ultrasonic signals through the liquid 106 and into the canister 80 and combustor casing 32. The ultrasonic transducer 124 detects reflected ultrasonic signals from the canister 80 and combustor casing 32 and supplies ultrasonic signals to the ultrasonic signal analyser 134 via the ultrasonic signal pulser and receiver 130. The ultrasonic signal analyser 134 stores the ultrasonic signals.

The carriage 114 is repeatedly moved along the tracks 116 and 118 on the frame 108 and the turntable 110 is rotated for one complete revolution so that the ultrasonic inspector 124 ultrasonically inspects all the radial positions R3 to Rx at the end of the canister 80 and the ultrasonic signal analyser 134 stores the ultrasonic signals.

The controller 138 sends signals to the motors 120 and/or 122 such that the carriage 114 is moved along the tracks 116 and 118 on the frame 108 so that the carriage 114 and transducer 124 are at a radial position greater than the radius of the radially outer external surface canister 80. The controller 138 sends signals to the motor 128 such that the member 126 is moved relative to the frame 108 so that the transducer 124 is at a first axial position $A_1$ on the radially outer external surface canister 80. The controller 138 sends signals to the motor 112 such that the turntable 110 is rotated about its axis of rotation R for one complete revolution while the carriage 114 and transducer 124 are at the first axial position $A_1$ on the radially outer external surface of the canister 80. During the rotation of the turntable 110 the ultrasonic transducer 124 is supplied with ultrasonic signals from the ultrasonic signal pulser and receiver 130 and the ultrasonic transducer 124 injects ultrasonic signals through the liquid 106 and into the canister 80. The ultrasonic transducer 124 detects reflected ultrasonic signals from the canister 80 and also from the combustor casing 32 within the canister 80 and supplies ultrasonic signals to the ultrasonic signal analyser 134 via the ultrasonic signal pulser and receiver 130. The ultrasonic signal analyser 134 stores the ultrasonic signals.

The controller 138 sends signals to the motor 128 such that the member 126 is moved relative to the frame 108 so that the ultrasonic transducer 124 is at a second axial position $A_2$ on the radially outer external surface of the canister 80 and the turntable 110 is rotated about its axis of rotation for one complete revolution while the carriage 114 and transducer 124 are at the second axial position $A_2$ on the radially outer external surface of the canister 80. During the rotation of the turntable 110 the ultrasonic transducer 124 is supplied with ultrasonic signals from the ultrasonic signal pulser and receiver 130 and the ultrasonic transducer 124 injects ultrasonic signals through the liquid 106 and into the canister 80 and combustor casing 32. The ultrasonic transducer 124 detects reflected ultrasonic signals from the canister 80 and combustor casing 32 and supplies ultrasonic signals to the ultrasonic signal analyser 134 via the ultrasonic signal pulser and receiver 130. The ultrasonic signal analyser 134 stores the ultrasonic signals.

The member 126 is repeatedly moved relative to the frame 108 and the turntable 110 is rotated for one complete revolution so that the ultrasonic inspector 124 ultrasonically inspects all the axial positions $A_3$ to $A_x$ on the radially outer external surface of the canister 80 and the ultrasonic signal analyser 134 stores the ultrasonic signals.

Similarly the ultrasonic transducer 124 may be/is moved over the radially inner external surface of the canister 80 and the ultrasonic signal analyser 134 stores the ultrasonic signals. The ultrasonic transducer 124 may be/is moved over the other axial end of the canister 80 and the ultrasonic signal analyser 134 stores the ultrasonic signals. The canister 80 may have to be inverted in order to ultrasonically inspect the other end of the canister 80.

The turntable 110 is rotated around its axis of rotation at a constant speed of rotation of between 5 rpm and 30 rpm preferably between 20 rpm and 30 rpm.

Figure 8:
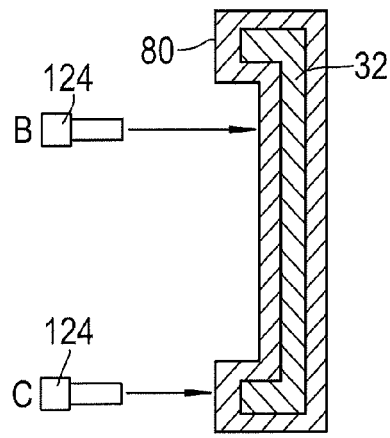
FIG. 8 is a cross-sectional view through a half of the canister and combustor casing showing the ultrasonic transducer at two positions relative to the canister and combustor casing.
Figure 9:
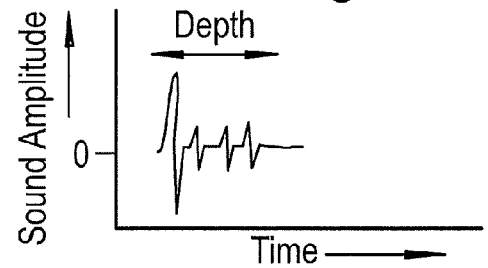
FIG. 9 is a display showing the sound amplitude against time of the detected ultrasonic signal for position B in FIG. 8.
Figure 10:
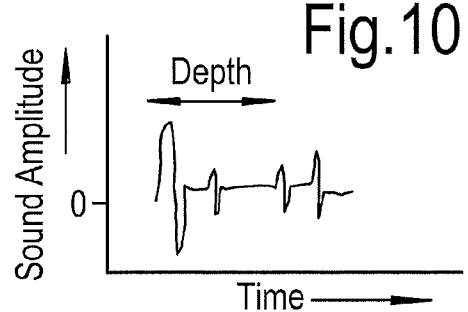
FIG. 10 is a display showing the sound amplitude against time of the detected ultrasonic signal for position C in FIG. 8.

A half cross-sectional view through the canister 80 and combustor casing 32 is shown in FIG. 8 and the ultrasonic transducer 124 shown at two axial positions B and C relative to the canister 80. FIGS. 9 and 10 show the ultrasonic sound amplitude against time at the two positions B and C, and it is seen that in each case there is a largest peak corresponding to the radially outer exterior surface of the canister 80, a first smaller peak corresponding to an interface between the canister 80 and the combustor casing 32, a second smaller peak corresponding to an interface between the canister 80 and the combustor casing 32 and a next largest peak corresponding to the radially inner exterior surface of the canister 80. It is to be noted that the time between the largest peak and the first smaller peak corresponds to the distance between the radially outer exterior surface of the canister 80 and the interface between the canister 80 and the combustor casing 32 and the time between the second smaller peak and the next largest peak corresponds to the distance between the interface between the canister 80 and the combustor casing 32 and the radially inner exterior surface of the canister 80. These distances are calculated using the known, or measured, velocity of the ultrasonic signal in the canister 80.

Figure 11:
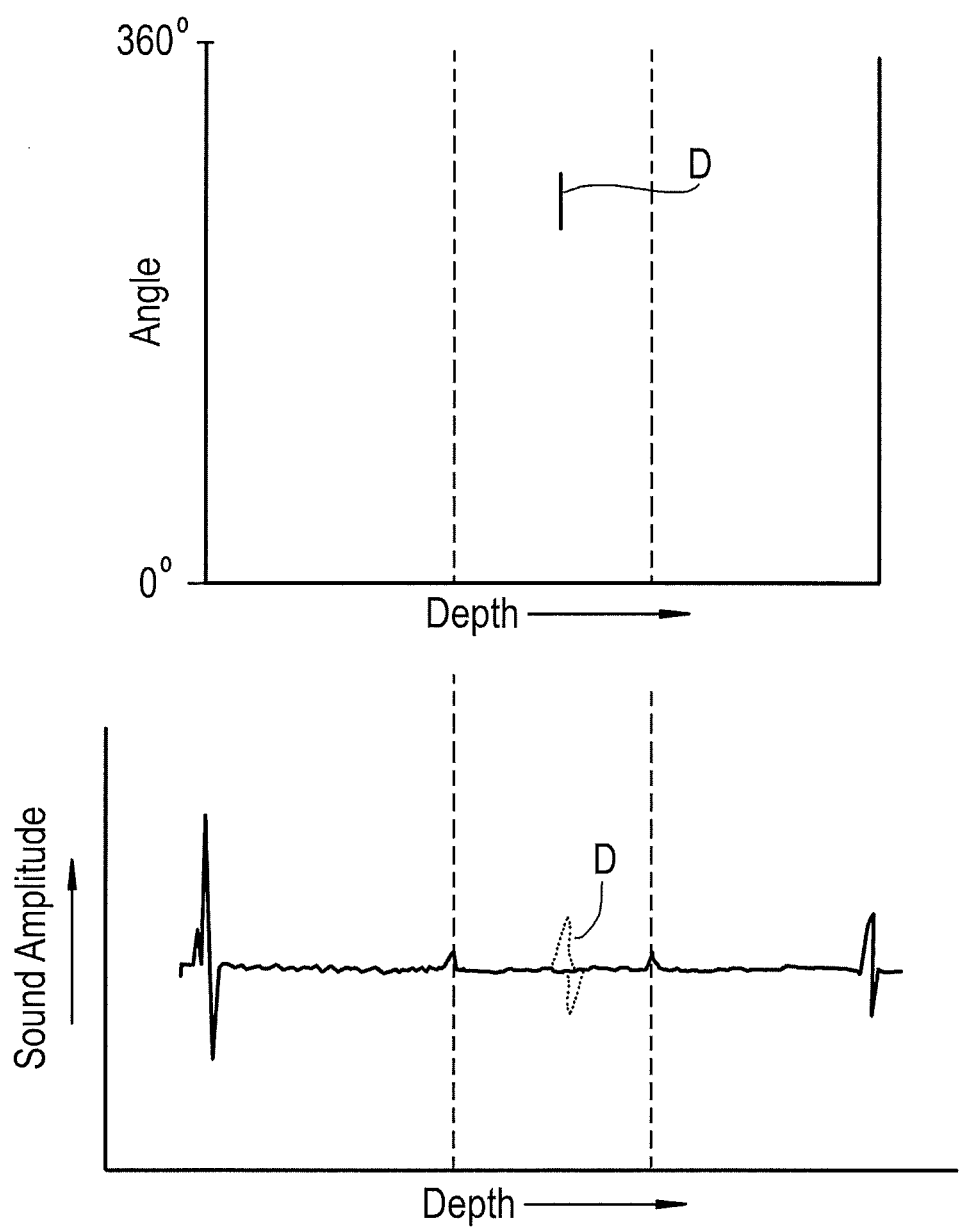
FIG. 11 is a display showing the sound amplitude against time of the detected ultrasonic signal for a full circumferential inspection at axial position B and a defect at one circumferential position at axial position B of FIG. 8.

The ultrasonic signal analyser 134 stores and analyses all the detected ultrasonic signals from the ultrasonic transducer 124. The ultrasonic signal analyser 134 manipulates the ultrasonic signals and displays the ultrasonic signals on the display 134. The ultrasonic signal is displayed on the display 134 as a chart of rotational position against time with ultrasonic signal amplitude displayed as a grey scale or artificial colour for each scan increment, as shown in FIG. 11. The ultrasonic signal analyser 134 analyses the ultrasonic signals and differentiates by separation of ultrasonic signals with and without rotational symmetry, highlighting ultrasonic signals that have no rotational symmetry and have an amplitude above a predetermined amplitude as a potential defect, such as a region of incomplete consolidation, an inclusion, a crack, a fissure or a flaw etc, D in FIG. 11. Geometric features, such as changes in cross-sectional thickness, in the component have rotational symmetry. A defect, such as a region of incomplete consolidation, an inclusion, a crack, a fissure or a flaw etc, D in the combustion casing 32 however occurs at a discrete location in the combustion casing 32 and therefore lacks rotational symmetry and is easily distinguished.

The ultrasonic signal analyser 134 analyses the ultrasonic signals and determines the thickness of the canister 80 at each position on the surface of the canister 80. The ultrasonic signal analyser 134 analyses the ultrasonic signals and determines the thickness of the canister 80 at all positions circumferentially around the canister 80 for each axial position of the canister 80 and for both of the radially inner outer external surface and the radially outer external surface of the canister 80. The ultrasonic signal analyser 134 analyses the ultrasonic signals and determines the thickness of the canister 80 at all positions circumferentially around the canister 80 for each radial position of the canister 80 and for both of the axial ends of the canister 80.

Figure 12:
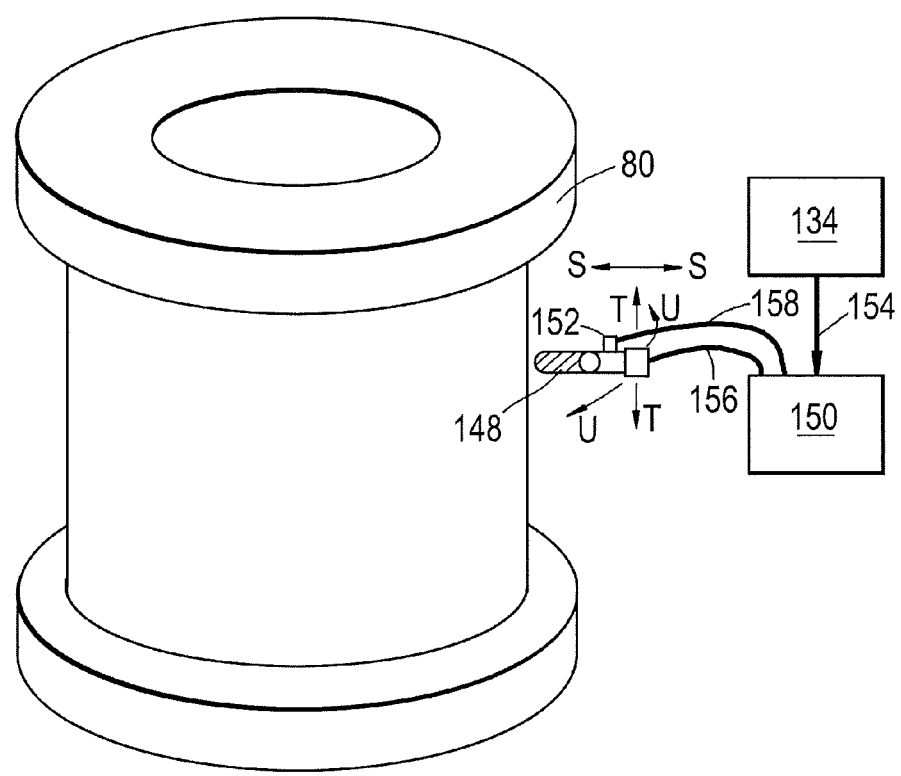
FIG. 12 is a cross-sectional view through a half of the canister and combustor casing showing an apparatus comprising ultrasonic transducer arrays to transmit and receive ultrasonic signals.

The ultrasonic signal processor 134 sends the data for the thickness of the canister 80 at each position on the surface of the canister 80, this corresponds to the distance between the interface between the canister 80 and the combustor casing 32 and the surface of the canister 80 at each position on the surface of the canister 80, to a control system 150 for a machining tool 148 via a cable 154, as shown in FIG. 12. The canister 80 is then removed from the powder metal combustor casing 32 by machining the canister 80. The control system 150 for the machining tool 148 controls the movement of the machining tool 148 over the canister 80 such that at each position of the canister 80 the machining tool 148 removes the determined thickness of the canister 80 for the corresponding position on the external surface of the canister 80. The machining of the canister 80 may be by any suitable machining tool or suitable combination of machining tools and for example comprises a milling tool or a grinding tool. The machining tool 148 may be a multi-axis machining tool. The canister 80 and article 32 may remain in a fixed position while the machining tool 148 is movable towards and away S from the canister 80, axially along T the canister 80 and circumferentially around U the canister 80 as shown in FIG. 12 to machine the exterior surfaces at both axial ends of the canister 80 and the radially inner and outer external surfaces of the canister 80. Alternatively, the canister 80 may be rotatably mounted on its axis and the machining tool 148 is movable towards and away S from the canister 80 and axially along T the canister 80 as shown in FIG. 12 to machine the exterior surfaces at both axial ends of the canister 80 and the radially inner and outer external surfaces of the canister 80.

The data for the thickness of the canister 80 at each position on the surface of the canister 80 would be in the form of coordinates relative to a known datum position or known geometrical datum location provided on the canister 80. The machining of the canister 80 may also involve the machining of an inter-diffusion region, a region where there is inter-diffusion of atoms between the canister 80 and the combustor casing 32, between the combustor casing 32 and the canister 80.

The machining tool 148 may be provided with one or more sensors 152, e.g. electromagnetic sensors, vibration sensors or force feedback sensors, arranged to send feedback signals to the control system 150 for the machining tool 148 via a cable 158. The control system 150 for the machining tool 148 is arranged to analyse the feedback signals to determine the distance to the interface between the canister 80 and the combustor casing 32, e.g. the thickness of the canister 80, and to compare the thickness of the canister 80 at each position on the surface of the canister 80 as determined by the ultrasonic signal processor 134 with the thickness of the canister 80 at the same position on the surface of the canister 80 as determined by the control system 150 for the machining tool 148 to validate the thickness of the canister 80 at each position on the surface of the canister 80 and if necessary adjusting the control of the machining tool 148 such that the appropriate amount of material is removed from the canister 80 to reach the interface between the canister 80 and the combustor casing 32.

The combustor casing 32 is a net shape article which only requires a minor amount of machining to provide the apertures 42 through bosses 43 and/or the apertures 39 and 41 through the flanges 38 and 40 respectively and finish machining of the bosses and flanges 38 and 40 etc. The machining of the combustor casing 32 may be by any suitable machining tool and for example the apertures are produced using a drill or a drill and a tapper and for example the finish machining tool comprises a milling tool.

Figure 13:
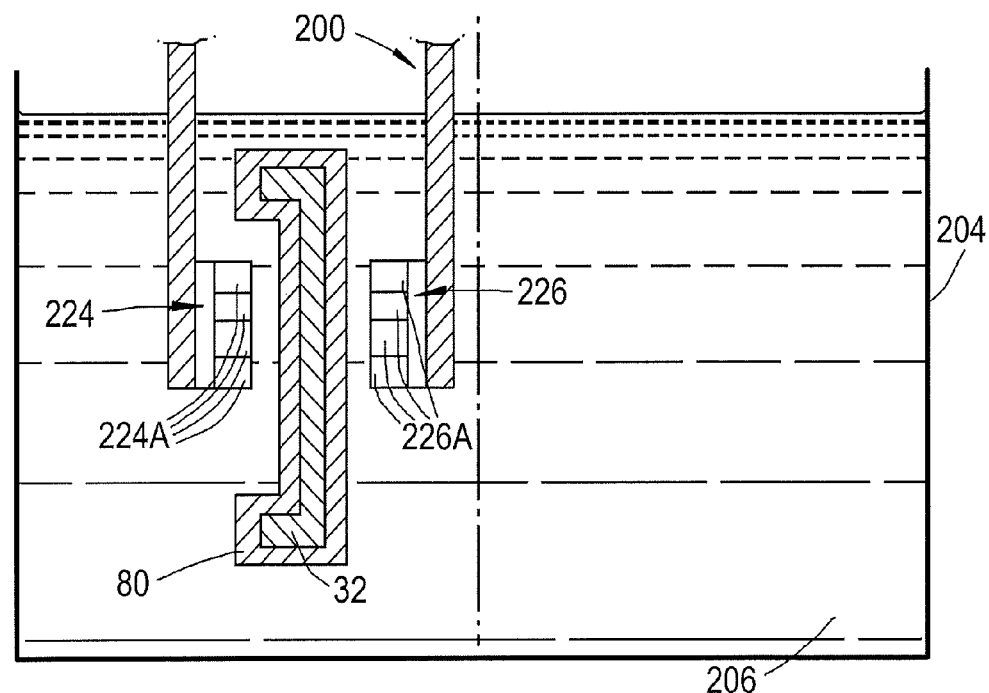
FIG. 13 is a perspective view of an apparatus for machining the canister from an ultrasonically inspected combustor casing.

FIG. 13 shows the canister 80 and combustor casing 32 and a further ultrasonic inspection apparatus 200 comprising a first ultrasonic transducer 224 and a second ultrasonic transducer 226 arranged in a tank 204 containing water 206. The first ultrasonic transducer 224 is a multiple element array transducer 224A arranged to transmit ultrasonic signals into the canister 80 spaced radially outwardly of the radially outer exterior surface of the canister 80. The second ultrasonic transducer 226 is a multiple element array transducer 226A arranged to receive ultrasonic signals transmitted through the canister 80 spaced radially inwardly of the radially inner exterior surface of the canister 80. The advantage of the multiple element array transducers 224A, 226A is that wide areas may be scanned in a volumetric method whilst minimising the actual movement of the ultrasonic transducers 224 and 226. The ultrasonic signals are directed through constructive interference of phased pulses. The ultrasonic transducer 224 and/or 226 may be a multiple element one dimensional array transducer, or a multiple element two dimensional array transducer, in which individual elements are pulsed in sequence and the ultrasonic signals combine constructively, or destructively, to produce a resulting primary single ultrasonic signal wave front. The multiple element one dimensional array transducer, or a multiple element two dimensional array transducer, receive the ultrasonic signal and spatially sort the returning ultrasonic signal wave front in terms of arrival time and amplitude at each individual element to facilitate analysis.

Although the present invention has been described with reference to a combustor casing it is equally possible for the present invention to be a fan casing, a compressor casing or a turbine casing or a combined combustor and turbine casing for a gas turbine engine or other turbomachine.

Although the present invention has been described with reference to a combustor casing it is equally possible for the present invention to be any other article and the article may have any shape. For example the article may be a flanged tube, a pressure vessel or a bearing. The article may be a gas turbine engine, or a turbomachine, bladed disc (blisk), disc or drum and may be a fibre reinforced bladed disc, disc or drum.

Although the present invention has been described with reference to manufacturing an article from powder material in a canister the present invention is equally applicable to manufacturing an article by diffusion bonding two or more components together in a canister or to manufacturing an article by consolidating and diffusion bonding powder material and at least one component together in a canister.

The hot pressing may comprise hot isostatic pressing. The hot pressing may occur at a temperature in the range of 800 to 950° C. and a pressure of at least 70 MPa.

The powder material may comprise a powder metal or powder alloy.

The component may be a metal or an alloy. The component may be a wire or a block, e.g. a metal wire, an alloy wire, a metal block or an alloy block. The block may have been previously formed from powder material, e.g. from powder metal or powder alloy.

The powder material and the component may have the same composition.

The powder material may be a nickel alloy, a titanium alloy, a ferritic steel, an austenitic stainless steel or a duplex stainless steel. The component may be a nickel alloy, a titanium alloy, a ferritic steel, an austenitic stainless steel or a duplex stainless steel.

The powder metal may be nickel, titanium, copper or aluminium. The component may be nickel, titanium, copper or aluminium.

The powder material may be a combination of two or more metals or two or more alloys or a combination of an alloy and a metal to form a bi-metallic, e.g. a copper and aluminium bi-metallic.

Reinforcing fibres may be provided in the canister with the powder material to form a fibre reinforced article. Reinforcing fibres may be provided in the canister with at least one wire to form a fibre reinforced article. The fibre reinforced article may comprise a metal matrix composite, e.g. a titanium metal matrix composite, or a ceramic matrix composite.

The canister may be formed from steel, preferably mild steel or low carbon steel. Most preferably the canister is formed from stainless steel because stainless steels have low carbon levels, are rust resistant and have reduced inter-diffusion.

The ultrasonic transducer may be a piezoelectric transducer and these operate as both a transmitter and a receiver as discussed above. Other types of ultrasonic transducer may be used, the ultrasonic transducer may be magnetostrictive transducer (EMAT—electromagnetic acoustic transducer) or a laser may be used to generate an ultrasonic signal and an interferometer is used to detect the ultrasonic signal. The present invention has been described with reference to immersing the canister in a liquid, water, tank to perform the ultrasonic inspection because ultrasonic signals transmit more efficiently through liquid, water, than air. However, water jet ultrasonic transducers, or water jet probes, may be used instead of a liquid tank or indeed the ultrasonic inspection may take place in air. The ultrasonic transducer may transmit ultrasonic signals and receive ultrasonic signals reflected back to the ultrasonic transducer as described above or a first ultrasonic transducer may transmit ultrasonic signals and a second ultrasonic transducer may receive ultrasonic signals transmitted from the first ultrasonic transducer. The ultrasonic transducers are arranged to operate at frequencies in the range of 1 to 40 MHz. The EMAT ultrasonic transducers do not require water, or other liquid, as a coupling between the transducers and the canister and an associated tank if a steel, mild steel, low carbon steel or stainless steel, canister is used. The use of a laser is possible because the canister provides a surface which may be ablated by the laser to produce the ultrasonic signal without damaging the article within the canister. A secondary advantage of the water and water tank is that the water stabilises the temperature, e.g. maintains a constant temperature, during ultrasonic inspection.

The ultrasonic transducers are arranged to provide large quantities of information, data, to ensure adequate resolution on a fine scale at all locations within the article. There may be one or more specific regions within the article which require more information, data, these may include locations of the article which will be subject to high mechanical loads or high stress intensity in operation, for example wall section thickness and the position of bosses on the casing relative to the datum location. The present invention may construct a virtual model of the article, the interface between the article and the canister from the information, data, from this ultrasonic scanning. The virtual model may indicate or identify regions of the article which have different densities and/or thickness. The virtual model of the article and the canister may be divided into volumetric elements, termed voxels or volumetric pixels. The size of the voxels may vary. A target maximum resolution of the voxels is voxels with sides of 100 μm. The ultrasonic transducers may be used to scan the article within the canister from multiple, different orientations and the scans are cross-referenced to minimise the uncertainty, or increase the accuracy, of the ultrasonic scanning. The ultrasonic signal timings, phase shifts and amplitudes provide information about the standard, quality, of the consolidation of the powder material, the thickness of the article, the position of the article relative to the canister, the position of the interface between the article and the canister, and the thickness of the canister.

An advantage of the present invention is that the position of the interface between the canister and the article after consolidation of the powder material is determined accurately from the ultrasonic inspection of the article within the canister. A further advantage of the present invention is that the position of the interface between canister and the article is used to determine the thickness of the canister and the thickness of the canister is used as an input to control a machining tool used to remove the canister from the article so as not to damage the article. A further advantage of the present invention is that if unacceptable defects are detected in the article after consolidation of the powder material the article may be rejected and the expense of machining the canister from the article may be saved. Non-compliance of the article may be detected at an earlier stage in the manufacturing process. Another advantage of the present invention is that the canister may be removed from the article using machining dispensing with the requirement to use acids which may damage the article and which may be subject to environmental legislation. Another advantage of the present invention is that in some instances it is easier to machine the canister than to machine the article, for example it is easier to machine a steel canister than to machine a nickel base superalloy article, because the steel canister is not as hard as the nickel base superalloy and hence cheaper machine tools are required to machine the canister than the nickel base superalloy article. The article may be machined closer to the desired wall thickness, or dimensions, reducing the weight of the article. Another advantage is that it is possible to determine if any reinforcing fibres are located in the correct position within the article if the article is fibre reinforced.

The invention claimed is:

1. A method of manufacturing an article by hot pressing and ultrasonically inspecting the article comprising the steps of:—
   (a) forming a canister,
   (b) filling the canister with powder material, filling the canister with a plurality of components or filling the canister with powder material and at least one component,
   (c) evacuating the canister,
   (d) sealing the evacuated canister,
   (e) applying heat and pressure to the canister to consolidate and diffusion bond the powder material together to form the article, to diffusion bond the components together to form the article or to consolidate the powder material and diffusion bond the powder material and the at least one component together to form the article,
   (f) ultrasonically inspecting the article within the canister by moving at least one ultrasonic transducer over the whole of an external surface of the canister,
   (g) determining the position of an interface between the article and the canister at each position on the external surface of the canister,
   (h) determining if there are any defects within the article,
   (i) determining the thickness of the canister at each position on the surface of the canister,
   (j) removing the canister from the article by machining the canister using a machine tool, and
   (k) controlling the movement of the machine tool over the canister such that at each position of the canister the machine tool removes the determined thickness of the canister for the corresponding position on the external surface of the canister.

2. A method as claimed in claim 1 wherein step (e) comprises hot isostatic pressing.

3. A method as claimed in claim 2 wherein step (e) comprises hot isostatic pressing at a temperature in the range of 800 to 950° C. and a pressure of at least 70 MPa.

4. A method as claimed in claim 1 wherein step (j) comprises machining the canister from the article using a milling tool and/or a grinding tool.

5. A method as claimed in claim 1 wherein the powder material is selected from the group consisting of a powder metal and a powder alloy.

6. A method as claimed in claim 1 wherein the component is selected from the group consisting of a metal and an alloy.

7. A method as claimed in claim 6 wherein the component is selected from the group comprising at least one wire and at least one block.

8. A method as claimed in claim 1 wherein the powder material and the component have the same composition.

9. A method as claimed in claim 5 wherein the powder material is selected from the group consisting of nickel, titanium, copper, a nickel alloy, a titanium alloy, a ferritic steel, an austenitic stainless steel and a duplex stainless steel.

10. A method as claimed in claim 6 wherein the component is selected from the group consisting of nickel, titanium, copper, aluminium, a nickel alloy, a titanium alloy, a ferritic steel, an austenitic stainless steel and a duplex stainless steel.

11. A method as claimed in claim 5 wherein the powder material is a selected from the group consisting of a combination of two or more metals, a combination of two or more alloys and a combination of an alloy and a metal, to form a bi-metallic.

12. A method as claimed in claim 1 wherein step (b) comprises providing reinforcing fibres in the canister with the powder material and step (e) comprises forming a fibre reinforced article.

13. A method as claimed in claim 7 wherein step (b) comprises providing reinforcing fibres in the canister with the at least one wire and step (e) comprises forming a fibre reinforced article.

14. A method as claimed in claim 12 wherein the fibre reinforced article is a metal matrix composite.

15. A method as claimed in claim 1 wherein step (f) comprises providing a single ultrasonic transducer, transmitting an ultrasonic signal from the ultrasonic transducer through the canister into the article and receiving an ultrasonic signal returning from the article through the canister at the single ultrasonic transducer.

16. A method as claimed in claim 1 wherein step (f) comprises providing a first ultrasonic transducer and a second ultrasonic transducer, transmitting an ultrasonic signal from the first ultrasonic transducer through the canister into the article and receiving an ultrasonic signal from the article through the canister at the second ultrasonic transducer.

17. A method as claimed in claim 16 wherein step (f) comprises providing a first ultrasonic transducer comprising a multiple element one dimensional array transducer and a second ultrasonic transducer comprising a multiple element one dimensional array transducer or a first ultrasonic transducer comprising a multiple element two dimensional array transducer and a second ultrasonic transducer comprising a multiple element two dimensional array transducer.

18. A method as claimed in claim 1 wherein step (f) comprises providing a piezoelectric transducer or a magnetostrictive transducer.

19. A method as claimed in claim 1 wherein step (f) comprises using frequencies in the range of 1 to 40 MHz.

20. A method as claimed in claim 1 wherein step (k) comprises providing a feedback sensor on the machining tool.

21. A method as claimed in claim 1 wherein the article is selected from the group consisting of a gas turbine engine and a turbomachine casing.

22. A method of inspecting and removing an article produced by hot pressing from a canister comprising the steps of:—
  (a) ultrasonically inspecting an article produced by hot pressing within a canister by moving at least one ultrasonic transducer over the whole of an external surface of the canister,
  (b) determining the position of an interface between the article and the canister at each position on the external surface of the canister,
  (c) determining if there are any defects within the article,
  (d) determining the thickness of the canister at each position on the surface of the canister,
  (e) removing the canister from the article by machining the canister using a machine tool, and
  (f) controlling the movement of the machine tool over the canister such that at each position of the canister the machine tool removes the determined thickness of the canister for the corresponding position on the external surface of the canister.

* * * * *